(12) United States Patent
Hodgson et al.

(10) Patent No.: US 6,573,066 B1
(45) Date of Patent: Jun. 3, 2003

(54) **FTSH FROM *STAPHYLOCOCCUS AUREUS***

(75) Inventors: John Edward Hodgson, Malvern, PA (US); Owen Jenkins, Roydon Essex (GB); Gillian Sarginson, Tadworth (GB)

(73) Assignees: SmithKline Beecham Corporation, Philadelphia, PA (US); SmithKline Beecham plc, Brentford (GB)

( * ) Notice: Subject to any disclaimer, the term of this patent is extended or adjusted under 35 U.S.C. 154(b) by 615 days.

(21) Appl. No.: 08/816,177

(22) Filed: Mar. 12, 1997

(30) Foreign Application Priority Data

Mar. 14, 1996 (GB) .............................................. 9605381

(51) Int. Cl.$^7$ .......................... C12P 21/06; C12N 15/00; C12N 1/20; C07H 21/04
(52) U.S. Cl. ................... 435/69.1; 435/71.1; 435/252.3; 435/254.11; 435/320.1; 435/325; 536/23.7; 935/9; 935/11; 935/12; 935/22; 935/66
(58) Field of Search ............................... 536/23.1, 24.1, 536/23.7, 23.4; 435/320.1, 6, 69.1, 7.1, 69.3, 69.7, 70.1, 71.1, 71.2, 325, 252.3, 254.11; 530/350, 300, 825; 436/500; 935/9, 11, 12, 66, 22

(56) References Cited

U.S. PATENT DOCUMENTS 5,175,101 A  * 12/1992 Götz et al.

OTHER PUBLICATIONS

T. Ohta et al., Biochem. Biophys. Res. Commun. 193 (2): 730–737, 1993.*
P. Chetchotisakd et al. Clin Infectious Diseases 18(6): 929–937, 1994.*
R.D. Fleischmann et al. Science 269: 496–512, Jul. 1995.*
P. Hugueney et al. Proc. Natl. Acad. Sci. 92(12): 5630–5634, Jun. 1995.*
Nilsson et al, Microbiology 140:2601–2610, 1994.*
Wolfe, K., Cur. Genet, 25:379–383, 1994.*
American Type Culture Collection (ATCC) Catalogue of Bacteria and Bacteriophages, 17$^{th}$ Edition, 1989. p. 202–204, 1989.*
Boehringer Mannheim Biochemicals, Catalog p. 292, 1991.*
Stratagene, Product Catolog p. 66, 1991.*
GIBCO BRL, Catalogue and Reference Guide, p. 292, 1992.*
Promega, Catalog pp 90–91, 1993/1994.*
New England Biolabs, Catalog, pp 60–62, 1986/1987.*
Rudinger, in: Peptide Hormones, Univ.Park Press, pp. 1–7, 1976.*
Akiyama, et al., "FtsH (HflB) is an ATP–dependent Protease Selectivity Acting on SecY and Some Other Membrane Proteins,", *Journal of Biological Chemistry*, 271; pp. 31196–31201 (1996).
Akiyama, et al., "Subunit a of proton ATPase $F_0$ sector is a substrate of the FtsH protease in *Escheichia coli*", *FEBS Letters*, 399, pp. 26–28, (1996).

Ge, et al., "Sequencing, expression and genetic characterization of the *Helicobacter pylori ftsH* gene encoding a protein homologous to members of a novel putative ATPase family", *The Journal of Bacteriology*, 178, pp. 6151–6157 (1996).
Gottesman, S., "Proteases and Their Targets in *Escherichia Coli*", *Annual Review of Genetics*, 30, pp. 465–506 (1996.
Herman, et al., "Degradation of $^{32}$, the heat shock regulator in *Escherichia coli*, is governed by HflB", Proceedings of the National Acadamy of Sciences, 92, pp. 3516–3520 (1995).
Herman, et al., "The HflB Protease of *Escherichia coli* Degrades Its Inhibitor cIII", *The Journal of Bacteriology*, 179, pp. 385–386 (1997).
Kihara, et al., "FtsH is required for proteolytic elimination of uncomplexed forms of SecY, an essential protein translocase subunit", *Proceedings of the National Academy of Sciences USA*, 92, pp. 4532–4536 (1995).
Nilsson, et al., "A Lactococcus lactis gene encodes a membrane protein with putative ATPase activity that is homologous to the essential *Escherichia coli ftsH* gene product", *Microbiology* 140, pp. 2601–2610 (1994).
Ogasaware, et. al., "Systematic sequencing of the 180 kilobase region of the Bacillus subtilis chromosome containing the replication origin", *DNA Research*, 1, pp. 1–14 (1994).
Schnall, et al., "Identification of a set of yeast genes coding for a novel family of putative ATPases with high similarity to constiuents of the 26S protease complex", *Yeast*, 10, pp. 1141–1155 (1994).
Shotland, et al., "Proteolysis of the phage CII regulatory protein by FtsH (HflB) of *Escherichia coli*", *Molecular Microbiology*, 24, pp. 1303–1310 (1997).
Thorsness, et al., "Inactivation of YME1, a member of the ftsH–SEC18–Pas1–cdc48 family of putative ATPase–encoding genes, causes increased escape of DNA from mitochondria in *Saccharomyces cerevisiae*", *Molecular and Cellular Biology*, 13, pp. 5418–5426 (1993).
Tomoyasu, et al., "The *Escherichia coli* FtsH protein is a projaryotic member of a protein family o putative ATPases in involved in membrane functions, cell cycle control and gene expression", *Journal of Bacteriology*, 175, pp. 1344–1351 (1993).
Tomoyasu, et al., "Topology and subcellular localization of FtsH protein in *Escherichia coli*", *Journal of Bacteriology*, 175, pp. 1253–1357 (1993).
Tomoyasu, et al., "*Escherichia coli* FtsH is a membrane–bound, ATP–dependent protease which degrades the heat–shock transcription factor 32", *The EMBO Journal*, 14, pp. 2551–2560 (1995).
Deuerling Elke, et al., "The ftsH Gene of *Bacillus Subtilis* is Involved in Major Cellular Process Such as Sporulation, Stress Adaptation and Secretion", *Mol. Microbiol.*, vol. 23, No. 5: pp. 921–933, (1997).

* cited by examiner

Primary Examiner—Patricia A. Duffy
(74) Attorney, Agent, or Firm—Jason C Fedon; Edward R Gimmi; Charles M. Kinzig

(57) ABSTRACT

The invention provides ftsH polypeptides, polynucleotides encoding ftsH polypeptides and related polynucleotides and methods for producing such polypeptides by recombinant techniques. Also provided are diagnostic methods for detecting *Staphylococcus aureus*.

27 Claims, No Drawings

FTSH FROM *STAPHYLOCOCCUS AUREUS*

RELATED APPLICATIONS

This application claims priority to UK provisional application number 9605381.4, filed Mar. 14, 1996.

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides of the ATPase family, hereinafter referred to as "FtsH".

BACKGROUND OF THE INVENTION

It is particularly preferred to employ Staphylococcal genes and gene products as targets for the development of antibiotics. The Staphylococci make up a medically important genera of microbes. They are known to produce two types of disease, invasive and toxigenic. Invasive infections are characterized generally by abscess formation effecting both skin surfaces and deep tissues. *S. aureus* is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

The frequency of *Staphylococcus aureus* infections has risen dramatically in the past 20 years. This has been attributed to the emergence of multiply antibiotic resistant strains and an increasing population of people with weakened immune systems. It is no longer uncommon to isolate *Staphylococcus aureus* strains which are resistant to some or all of the standard antibiotics. This has created a demand for both new anti-microbial agents and diagnostic tests for this organism.

FtsH, an essential membrane bound protein involved in membrane functions, cell cycle control and gene expression was initially characterised in *Escherichia coli* (Tomoyasu, T., Yuki, T., Morimura, S., Mori, H., Yamanaka, K., Niki, H., Hiraga, S. and Ogura, T. (1993) Journal of Bacteriology 175: 1344–1351). The *Escherichia coli* FtsH protein comprises 644 amino acid residues with a predicted molecular mass of 70.7 kDa. and has been shown to localise to the cytoplasmic membrane via two hydrophobic domains (Tomoyasu, T., Yamanaka, K., Murata, K., Suzaki, T., Bouloc, P., Kato, A., Niki, H., Hiraga, S. and Ogura, T. (1993) Journal of Bacteriology 175: 1352–1357). It belongs to a novel putative ATPase family known as the AAA-protein family, members of which are widely distributed among eubacteria, archaebacteria and eukaryotes (Kunau, W.H., Beyer, A., Franken, T., Gotte, K., Marzioch, M., Saidowski, J., Skaletz-Rorowski, A. and Wiebel, F. F. (1993) Biochemie 75: 209–224). FtsH demonstrates significant homology to these ATPases over a cytoplasmic region of some 200 amino acid residues which includes a putative ATP binding site, a zinc-binding motif and the adjacent C-terminal sequence. Recently, *Escherichia coli* FtsH was shown to catalyse the ATP dependent degradation of the (σ32 subunit of *Escherichia coli* RNA polymerase (Tomoyasu, T., Gamer, J., Bukau, B., Kanemori, M., Mori, H., Rutman, A. J., Oppenheim, A. B., Yura, T., Yamanaka, K., Niki, H., Hiraga, S. and Ogura, T. (1995) The EMBO Journal 14 2551–2560) and as such is thought to be a key element in transcriptional control. In addition, FtsH is required for the proteolytic elimination of uncomplexed forms of SecY, important in maintaining optimal protein translocation and integrity of the membrane (Kihara, A., Akiyama, Y., Ito, K. (1995) Proceedings of the National Academy of Sciences USA 92: 4532–4536). Overproduction of SecY in FtsH mutant cells has been shown to deleteriously effect cell growth and protein export.

In addition to *Escherichia coli* (Tomoyasu, T., Yuki, T., Morimura, S., Mori, H., Yamanaka, K., Niki, H., Hiraga, S. and Ogura, T. (1993) Journal of Bacteriology 175: 1344–1351), highly conserved FtsH homologues have been identified in *Lactococcus lactis* (Nilsson, D., Lauridsen, A. A., Tomoyasu, T. and Ogura, T. (1994) Microbiology 140: 2601–2610), *Bacillus subtilis*, (Ogasawara, N., Nakai, S. and Yoshikawa, H. (1994) DNA Research 1: 1–14), and *Saccharomyces cerevisiae* (Thorsness, P. E., White, K. H. and Fox, T. D. (1993) Molecular and cellular Biology 13: 5418–5426, Schnall, R., Mannhaupt, G., Stuka, R., Ehnle, S., Schwarzlose, C., Vetter, I. and Feldmann, H. (1994) Yeast 10 1141–1155) however with the exception of *Escherichia coli* FtsH, none of these proteins have been purified and studied biochemically. The high level of identity among diverse eubacteria and eukaryotes strongly suggests commonality of function. The ftsH gene is essential for cell viability in *Escherichia coli* (Tomoyasu, T., Yuki, T., Morimura, S., Mori, H., Yamanaka, K., Niki, H., Hiraga, S. and Ogura, T. (1993) Journal of Bacteriology 175: 1344–1351). Inhibitors of FtsH proteins would prevent bacteria from establishing and maintaining infection of the host by disrupting transcription and protein translocation, resulting in arrested growth and ultimately to cell death as the bacteria become susceptible to host defences and thereby have utility in anti-bacterial therapy.

Clearly, there is a need for factors, such as the novel compounds of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists which can play a role in preventing, ameliorating or correcting infections, dysfunctions or diseases.

The polypeptides of the invention have amino acid sequence homology to a known *Bacillus subtilis* FtsH protein.

SUMMARY OF THE INVENTION

It is an object of the invention to provide polypeptides that have been identified as novel FtsH polypeptides by homology between the amino acid sequence set out in Table 1 [SEQ ID NO:2] and a known amino acid sequence or sequences of other proteins such as *Bacillus subtilis* FtsH protein.

It is a further object of the invention to provide polynucleotides that encode FtsH polypeptides, particularly polynucleotides that encode the polypeptide herein designated FtsH.

In a particularly preferred embodiment of the invention the polynucleotide comprises a region encoding FtsH polypeptides comprising the sequence set out in Table 1[SEQ ID NO:1], or a variant thereof.

In another particularly preferred embodiment of the invention there is a novel FtsH protein from *Staphylococcus*

*aureus* comprising the amino acid sequence of Table 1 [SEQ ID NO:2], or a variant thereof.

In accordance with another aspect of the invention there is provided an isolated nucleic acid molecule encoding a mature polypeptide expressible by the *Staphylococcus aureus* WCUH 29 strain contained in NCIMB Deposit No. 40771.

A further aspect of the invention there are provided isolated nucleic acid molecules encoding FtsH, particularly *Staphylococcus aureus* FtsH, including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of FtsH and polypeptides encoded thereby.

Another aspect of the invention there are provided novel polypeptides of *Staphylococcus aureus* referred to herein as FtsH as well as biologically, diagnostically, prophylactically, clinically or therapeutically useful variants thereof, and compositions comprising the same.

Among the particularly preferred embodiments of the invention are variants of FtsH polypeptide encoded by naturally occurring alleles of the FtsH gene.

In a preferred embodiment of the invention there are provided methods for producing the aforementioned FtsH polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing FtsH expression, treating disease, for example, disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis), assaying genetic variation, and administering a FtsH polypeptide or polynucleotide to an organism to raise an immunological response against a bacteria, especially a *Staphylococcus aureus* bacteria.

In accordance with certain preferred embodiments of this and other aspects of the invention there are provided polynucleotides that hybridize to FtsH polynucleotide sequences, particularly under stringent conditions.

In certain preferred embodiments of the invention there are provided antibodies against FtsH polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypetide or polynucleotide by detecting the presence or absence of a signal generated from the binding or interaction of the compound with the polypeptide or polynucleotide.

In accordance with yet another aspect of the invention, there are provided FtsH agonists and antagonists, preferably bacteriostatic or bactericidal agonists and antagonists.

In a further aspect of the invention there are provided compositions comprising a FtsH polynucleotide or a FtsH polypeptide for administration to a cell or to a multicellular organism.

Various changes and modifications within the spirit and scope of the disclosed invention will become readily apparent to those skilled in the art from reading the following descriptions and from reading the other parts of the present disclosure.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A.M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, MD 20894; Altschul, S., et al., *J. Mol. Biol.* 215: 403–410 (1990).

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the termn "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formnation, demethylation, formation of covalent cross-links, formation of cysteine, formation of pyroglutamate, formylation, gamma-arboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., *Meth. Enzymol.* 182:626–646 (1990) and Rattan et al., *Protein Synthesis: Posttranslational Modifications and Aging*, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid due may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel FtsH polypeptides and polynucleotides as described in greater detail below. In particular, the invention relates to polypeptides and polynucleotides of a novel FtsH of *Staphylococcus aureus*, which is related by amino acid sequence homology to *Bacillus subtilis* FtsH polypeptide. The invention relates especially to FtsH having the nucleotide and amino acid sequences set out in Table 1 [SEQ ID NO:1] and Table 1 [SEQ ID NO:2] respectively, and to the FtsH nucleotide sequences of the DNA deposited in NCIMB Deposit No. 40771 and amino acid sequences encoded thereby.

TABLE 1

*Staphylococcus aureus* FtsH Polynucleotide and Polypeptide Sequences

FtsH polynucleotide sequence [SEQ ID NO: 1].

```
5'-1  ATGCAGAAAG CTTTTCGCAA TGTGCTAGTT ATCGTAATAA TAGGCGTTAT
  51  TATTTTTGGT CTATTTTCAT ATTTAAACGG TAATGGAAAT ATGCCGAAAC
 101  AGCTTACATA TAATCAATTT ACTGAGAAGT TGGAAAAAGG TGACCTTAAA
 151  ACTTTAGAAA TCCAACCACA ACAAAATGTC TATATGGTAA GTGGTAAAAC
 201  GAAAAATGAT GAAGACTATT CATCAACTAT TTTATATAAC AACGAAAAAG
 251  AATTACAAAA AATTACTGAT GCTGCTAAAA AGCAAAACGG TGTAAAATTA
 301  ACGATTAAAG AAGAAGAAAA ACAAAGTGTC TTTGTGAGTA TACTTTCAAC
 351  ATTAATTCCA GTTGTAGTCA TAGCGTTATT ATTTATTTTC TTCCTAAGCC
 401  AAGCACAAGG TGGCGGTAGT GGCGGTCGTA TGATGAACTT TGGTAAATCT
 451  AAAGCAAAAA TGTACGATAA TAATAAACGT CGTGTTCGTT TCTCTGATGT
 501  AGCAGGGGCA GATGAAGAAA AACAAGAATT AATTGAAATT GTTGATTTCT
 551  TGAAAGATAA TAAAAAATTC AAAGAAATGG GATCTAGGAT TCCTAAAGGT
 601  GTCTTACTTG TTGGACCTCC AGGTACTGGT AAAACATTAC TTGCTAGAGC
 651  GGTTGCAGGT GAAGCTGGCG CACCATTCTT CTCTATTAGT GGTTCAGACT
 701  TTGTAGAGAT GTTTGTTGGT GTTGGTGCGA GCCGTGTTCG TGACTTATTC
 751  GATAATGCTA AGAAAAACGC GCCTTGTATC ATCTTTATCG ATGAGATTGA
 801  TGCTGTTGGT CGTCAACGTG GTGCAGGTGT TGGTGGCGGT CATGATGAAC
 851  GTGAACAAAC CCTAAACCAA TTATTAGTTG AAATGGATGG TTTCGGTGAA
 901  AATGAAGGTA TCATTATGAT AGCTGCTACA AACCGTCCTG ATATCCTTGA
 951  CCCAGCCTTA TTACGTCCAG GTCGTTTTGA TAGACAAATT CAAGTTGGTC
1001  GTCCAGATGT GAAAGGCCGT GAAGCAATTC TTCATGTTCA TGCTAAAAAC
1051  AAACCACTTG ATGAAACGGT TGATTTAAAA GCAATTTCAC AACGTACACC
1101  TGGTTTCTCA GGTGCTGATT TAGAGAACTT ATTAAATGAA GCATCTTTAA
1151  TTGCTGTACG TGAAGGTAAA AAGAAAATTG ACATGAGAGA TATCGAAGAG
1201  GCAACGGATA GAGTTATAGC CGGACCTGCT AAGAAATCTC GAGTTATTTC
1251  TAAGAAAGAA CGTAATATTG TTGCTCATCA CGAAGCTGGT CATACAATTA
1301  TCGGTATGGT ACTTGATGAG GCAGAAGTAG TGCATAAAGT TACTATTGTT
1351  CCACGTGGAC AAGCAGGTGG TTATGCAATG ATGCTACCTA AACAAGATCG
1401  TTTCTTAATG ACTGAACAAG AGTTATTAGA TAAAATCTGT GGTTTACTTG
1451  GTGGACGTGT ATCAGAAGAT ATTAACTTTA ACGAAGTATC AACAGGTGCT
1501  TCAAATGACT TCGAACGTGC AACACAAATC GCACGCTCAA TGGTTACGCA
1551  ATATGGTATG AGTAAAAAAT TAGGACCATT ACAGTTCGGT CATAGCAATG
1601  GTCAAGTATT CTTAGGTAAA GATATGCAAG GTGAGCCTAA TTATTCAAGC
1651  CAAATCGCAT ATGAAATTGA TAAAGAAGTT CAACGAATCG TTAAAGAACA
1701  ATACGAACGT TGTAAACAAA TTTTATTAGA GCACAAAGAA CAATTAATTT
1751  TAATTGCTGA AACATTATTA ACAGAAGAAA CATTAGTTGC TGAACAAATT
1801  CAATCATTAT TCTACGAAGG TAAATTACCT GAAATTGATT ATGATGCAGC
1851  TAAAGTTGTT AAAGATGAAG ATTCTGAATT TAATGATGGT AAATTCGGTA
1901  AATCTTATGA AGAGATTCGT AAAGAGCAAT TAGAAGATGG ACAACGTGAC
1951  GAAAGTGAAG ATCGTAAAGA AGAAAAAGAT ATTGCTGAGG ATAAAAAGAA
2001  AGCTGATAAA TCTGATGAAA AAGATGAACC AGCACATCGA CAAGCCCCAA
2051  ATATCGAAAA ACCTTACGAT CCAAATCACC CAGACAATAA ATAA-3'
```

FtsH polypeptide sequence deducted from the polynucleotide sequence in this table [SEQ ID NO:2].

```
NH2-1 MQKAFRNVLV IVIIGVIIFG LFSYLNGNGN MPKQLTYNQF TEKLEKGDLK

51 TLEIQPQQNV YMVSGKTKND EDYSSTILYN NEKELQKITD AAKKQNGVKL

101 TIKEEEKQSV FVSILSTLIP VVVIALLFIF FLSQAQGGGS GGRMMNFGKS

151 KAKMYDNNKR RVRFSDVAGA DEEKQELIEI VDFLKDNKKF KEMGSRIPKG

201 VLLVGPPGTG KTLLARAVAG EAGAPFFSIS GSDFVEMFVG VGASRVRDLF

251 DNAKKNAPCI IFIDEIDAVG RQRGAGVGGG HDEREQTLNQ LLVEMDGFGE

301 NEGIIMIAAT NRPDILDPAL LRPGRFDRQI QVGRPDVKGR EAILHVHAKN

351 KPLDETVDLK AISQRTPGFS GADLENLLNE ASLIAVREGK KKIDMRDIEE

401 ATDRVIAGPA KKSRVISKKE RNIVAHHEAG HTIIGMVLDE AEVVHKVTIV

451 PRGQAGGYAM MLPKQDRFLM TEQELLDKIC GLLGGRVSED INFNEVSTGA

501 SNDFERATQI ARSMVTQYGM SKKLGPLQFG HSNGQVFLGK DMQGEPNYSS

551 QIAYEIDKEV QRIVKEQYER CKQILLEHKE QLILIAETLL TEETLVAEQI
```

```
-continued
601 QSLFYEGKLP  EIDYDAAKVV  KDEDSEFNDG  KFGKSYEEIR  KEQLEDGQRD

651 ESEDRKEEKD  IAEDKKEADK  SDEKDEPAHR  QAPNIEKPYD  PNHPDNK-COOH
```

Deposited materials

A deposit containing a *Staphylococcus aureus* WCUH 29 strain has been deposited with the National Collections of Industrial and Marine Bacteria Ltd. (NCIMB), 23 St. Machar Drive, Aberdeen AB2 1RY, Scotland on Sep. 11, 1995 and assigned NCIMB Deposit No. 40771. The *Staphylococcus aureus* strain deposit is referred to herein as "the deposited strain" or as "the DNA of the deposited strain."

The deposited material is a strain that contains the full length FtsH DNA, referred to as "NCIMB 40771" upon deposit. The sequence of the polynucleotides contained in the deposited material, as well as the amino acid sequence of the polypeptide encoded thereby, are controlling in the event of any conflict with any description of sequences herein.

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

A license may be required to make, use or sell the deposited materials, and no such hereby granted.

Polypeptides

The polypeptides of the invention include the polypeptide of Table 1 [SEQ ID NO:2] (in particular the mature polypeptide) as well as polypeptides and fragments, particularly those which have the biological activity of FtsH, and also those which have at least 70% identity to the polypeptide of Table 1 [SEQ ID NO:2] or the relevant portion, preferably at least 80% identity to the polypeptide of Table 1 [SEQ ID NO:2], and more preferably at least 90% similarity (more preferably at least 90% identity) to the polypeptide of Table 1 [SEQ ID NO:2] and still more preferably at least 95% similarity (still more preferably at least 95% identity) to the polypeptide of Table 1 [SEQ ID NO:2] and also include portions of such polypeptides with such portion of the polypeptide generally containing at least 30 amino acids and more preferably at least 50 amino acids.

A fragment is a variant polypeptide having an amino acid sequence that entirely is the same as part but not all of the amino acid sequence of the aforementioned polypeptides. As with FtsH polypeptides fragments may be "free-standing," or comprised within a larger polypeptide of which they form a part or region, most preferably as a single continuous region, a single larger polypeptide.

Preferred fragments include, for example, truncation polypeptides having a portion of the amino acid sequence of Table 1 [SEQ ID NO:2], or of variants thereof, such as a continuous series of residues that includes the amino terminus, or a continuous series of residues that includes the carboxyl terminus. Degradation forms of the polypeptides of the invention in a host cell, particularly a *Staphylococcus aureus*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of FtsH, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Staphylococcus aureus* or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

Polynucleotides

Another aspect of the invention relates to isolated polynucleotides that encode the FtsH polypeptide having the deduced amino acid sequence of Table 1 [SEQ ID NO:2] and polynucleotides closely related thereto and variants thereof.

Using the information provided herein, such as the polynucleotide sequence set out in Table 1 [SEQ ID NO:1], a polynucleotide of the invention encoding FtsH polypeptide may be obtained using standard cloning and screening methods, such as those for cloning and sequencing chromosomal DNA fragments from bacteria using *Staphylococcus aureus* WCUH 29 cells as starting material, followed by obtaining a full length clone. For example, to obtain a polynucleotide sequence of the invention, such as the sequence given in Table 1 [SEQ ID NO:1], typically a library of clones of chromosomal DNA of *Staphylococcus aureus* WCUH 29 in *E.coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotide set out in Table 1 [SEQ ID NO:1] was discovered in a DNA library derived from *Staphylococcus aureus* WCUH 29.

The DNA sequence set out in Table 1 [SEQ ID NO:1] contains an open reading frame encoding a protein having about the number of amino acid residues set forth in Table 1 [SEQ ID NO:2] with a deduced molecular weight that can be calculated using amino acid residue molecular weight values well known in the art. FtsH of the invention is structurally related to other proteins of the ATPase family, as shown by the results of sequencing the DNA encoding FtsH of the deposited strain. The protein exhibits greatest homology to *Bacillus subtilis* FtsH protein among known proteins. FtsH of Table 1 [SEQ ID NO:2] has about 67% identity over its entire length with the amino acid sequence of *Bacillus subtilis* FtsH polypeptide.

The invention provides a polynucleotide sequence identical over its entire length to the coding sequence in Table 1 [SEQ ID NO:1]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro- protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA tag (Wilson et al., *Cell* 37: 767. (1984). Polynucleotides of the invention also include, but are not limited to, polynucleotides comprising a structural gene and its naturally associated sequences that control gene expression.

The term "polynucleotide encoding a polypeptide" as used herein encompasses polynucleotides that include a sequence encoding a polypeptide of the invention, particularly a bacterial polypeptide and more particularly a polypeptide of the *Staphylococcus aureus* FtsH having the amino acid sequence set out in Table 1 [SEQ ID NO:2]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having the deduced amino acid sequence of Table 1 [SEQ ID NO:2]. Variants that are fragments of the polynucleotides of the invention may be used to synthesize full-length polynucleotides of the invention.

Further particularly preferred embodiments are polynucleotides encoding FtsH variants, that have the amino acid sequence of FtsH polypeptide of Table 1 [SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of FtsH.

Further preferred embodiments of the invention are polynucleotides that are at least 70% identical over their entire length to a polynucleotide encoding FtsH polypeptide having the amino acid sequence set out in Table 1 [SEQ ID NO:2], and polynucleotides that are complementary to such polynucleotides. Alternatively, most highly preferred are polynucleotides that comprise a region that is at least 80% identical over its entire length to a polynucleotide encoding FtsH polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by the DNA of Table 1 [SEQ ID NO:1].

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the hybridization support in 0.1 ×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 under stringent hybridization conditions with a probe having the sequence of said polynucleotide sequence set forth in SEQ ID NO:1 or a fragment thereof; and isolating said DNA sequence.

Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding FtsH and to isolate cDNA and genomic clones of other genes that have a high sequence similarity to the FtsH gene. Such probes generally will comprise at least 15 bases. Preferably, such probes will have at least 30 bases and may have at least 50 bases. Particularly preferred probes will have at least 30 bases and will have 50 bases or less.

For example, the coding region of the FtsH gene may be isolated by screening using the known DNA sequence provided in SEQ ID NO:1 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of SEQ ID NOS:1 and/or 2 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, host cells, expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as *streptococci, staphylococci, enterococci E. coli, streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the FtsH polynucleotides of the invention for use as diagnostic reagents. Detection of FtsH in a eukaryote, particularly a mammal, and especially a human, will provide a diagnostic method for diagnosis of a disease. Eukaryotes (herein also "individual(s)", particularly mammals, and especially humans, infected with an organism comprising the FtsH gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled FtsH polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science*, 230: 1242 (1985). Sequence changes at specific locations also may be revealed by nuclease protection assays, such as RNase and S1 protection or a chemical cleavage method. See, e.g., Cotton et al., *Proc. Natl. Acad. Sci., USA*, 85: 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to a nucleic acid encoding FtsH can be used to identify and analyze mutations. These primers may also be used for amplifying FtsH DNA isolated from a sample derived from an individual. The invention further provides these primers with 1, 2, 3 or 4 nucleotides removed from the 5' and/or the 3' end. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by *Staphylococcus aureus*, and most preferably disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis), comprising determining from a sample derived from an individual a increased level of expression of polynucleotide having the sequence of Table 1 [SEQ ID NO:1]. Increased or decreased expression of FtsH polynucleotide can be measured using any on of the methods well known in the art for the quantitation of polynucleotides, such as, for example, amplification, PCR, RT-PCR, RNase protection, Northern blotting and other hybridization methods.

In addition, a diagnostic assay in accordance with the invention for detecting over-expression of FtsH protein compared to normal control tissue samples may be used to detect the presence of an infection, for example. Assay techniques that can be used to determine levels of a FtsH protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495–497 (1975); Kozbor et al., *Immunology Today* 4: 72 (1983); Cole et al., pg. 77–96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-FtsH or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against FtsH- polypeptide may be employed to treat infections, particularly bacterial infections and especially disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH).

Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody, for example as described in Jones, P. et al. (1986), Nature 321, 522–525 or Tempest et al.,(1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., J Biol Chem. 1989: 264,16985), coprecipitation of DNA with calcium phosphate (Benvenisty & Reshef, PNAS, 1986:83, 9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS 1984:81, 5849).

Antagonists and agonists—assays and molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The invention also provides a method of screening compounds to identify those which enhance (agonist) or block (antagonist) the action of FtsH polypeptides or polynucleotides, particularly those compounds that are bacteriostatic and/or bactericidal. The method of screening may involve high-throughput techniques.For example, to screen for agonists or antagonists a synthetic reaction mix, a cellular compartment, such as a membrane, cell envelope or cell wall, or a preparation of any thereof, comprising FtsH polypeptide and a labeled substrate or ligand of such polypeptide is incubated in the absence or the presence of a candidate molecule that may be a FtsH agonist or antagonist. The ability of the candidate molecule to agonize or antagonize the FtsH polypeptide is reflected in decreased binding of the labeled ligand or decreased production of product from such substrate. Molecules that bind gratuitously, i.e., without inducing the effects of FtsH polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in FtsH polynucleotide or polypeptide activity, and binding assays known in the art.

Another example of an assay for FtsH antagonists is a competitive assay that combines FtsH and a potential antagonist with FtsH-binding molecules, recombinant FtsH binding molecules, natural substrates or ligands, or substrate or ligand mimetics, under appropriate conditions for a competitive inhibition assay. FtsH can be labeled, such as by radioactivity or a colorimetric compound, such that the number of FtsH molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing FtsH-induced activities, thereby preventing the action of FtsH by excluding FtsH from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION, CRC* Press, Boca Raton, Fla. (1988), for a description of these molecules). Preferred potential antagonists include compounds related to and variants of FtsH.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block FtsH protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial FtsH proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

Vaccines

Another aspect of the invention relates to a method for inducing an immunological response in an individual, particularly a mammal which comprises inoculating the individual with FtsH, or a fragment or variant thereof, adequate to produce antibody and/or T cell immune response to protect said individual from infection, particularly bacterial infection and most particularly *Staphylococcus aureus* infection. Also provided are methods whereby such immunological response slows bacterial replication. Yet another aspect of the invention relates to a method of inducing immunological response in an individual which comprises delivering to such individual a nucleic acid vector to direct expression of FtsH, or a fragment or a variant thereof, for expressing FtsH, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a FtsH or protein coded therefrom, wherein the composition comprises a recombinant FtsH or protein coded therefrom comprising DNA which codes for and expresses an antigen of said FtsH or protein coded therefrom. The immunological response may be used therapeutically or prophylactically and may take the form of antibody immunity or cellular immunity such as that arising from CTL or CD4+T cells.

A FtsH polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Staphylococcus aureus* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular; intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain FtsH protein, it is to be understood that this covers fragments of the naturally occurring protein and similar proteins with additions, deletions or substitutions which do not substantially affect the immunogenic properties of the recombinant protein.

Compositions, kits and administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially Staphylococcus aureus wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 µg/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

EXAMPLES

The examples below are carried out using standard techniques, which are well known and routine to those of skill in the art, except where otherwise described in detail. The examples are illustrative, but do not limit the invention.

Example 1 Strain Selection, Library Production and Sequencing

The polynucleotide having the DNA sequence given in SEQ ID NO:1 was obtained from a library of clones of chromosomal DNA of Staphylococcus aureus in E. coli. The sequencing data from two or more clones containing overlapping Staphylococcus aureus DNAs was used to construct the contiguous DNA sequence in SEQ ID NO:1. Libraries may be prepared by routine methods, for example: Methods 1 and 2 below.

Total cellular DNA is isolated from Staphylococcus aureus WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and E.coli infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl2351I), and such fragments are size-fractionated according to standard procedures. EcoRI linkers are ligated to the DNA and the fragments then ligated into the vector Lambda ZapII that have been cut with EcoRI, the library packaged by standard procedures, and E.coli infected with the packaged library. The library is amplified by standard procedures.

Example 2 FtsH for Compound Screening

This invention provides a method of screening drugs to identify those which interfere with the mechanism of action of the FtsH protein such that it is inhibited, the method comprising contacting the FtsH protein with the drug and measuring the inhibition of FtsH activity. The polypeptide in any of the forms described above, purified using any of the methods described above, can be used to configure an in vitro assay based on its mechanism of action, for example in the presence of purified bacterial membranes or vesicles or synthetic phospholipid membrane mimics or in the appropriate enzyme buffer if membranes are not required and including the incorporation of additional macromolecular or low molecular weight cofactors which are either necessary for, or potentate, the activities of FtsH protein.

Examples of assays relating to the invention are set forth below:

(1) Proteolytic activity. The measurement of the cleavage of peptide bonds within peptide or protein substrates or amide or ester bonds within model substrates (e.g. Antonov, V.K. Chemistry of Proteolysis [1993] Springer Verlag, Berlin) provides a primary assay format. Substrates may be in the form of any peptide based molecule which is capable of cleavage by FtsH. Cleavage of proteins and/or peptides may be monitored using a number of approaches including, but not limited to, chromatographic separation of substrate from products (e.g. by reverse-phase, size exclusion, hydrophobic interaction, affinity or ion exchange chromatography) or using extrinsically labeled substrate (e.g. radioactive or optical label). In the latter case, measurements may be based on either the physical separation of products from substrate (e.g. by precipitation and/or filtration) or, in homogeneous assay formats, on proximity or environmental effects on the label (e.g. scintillation proximity, fluorescence energy transfer, fluorescence anisotropy, fluorescence correlation fluctuations, environmental changes in fluorescence intensity and/or wavelength).

(2) Protein: Protein Interactions: The measurement of the interaction of FtsH protein with additional proteins or peptides, either within a lipid-based membrane system or in solution, provides for a potential assay format. Heterogeneous assays encompassing the use of an immunoassay or surface-coating format in conjunction with either radiolabelled or optically labeled proteins and components are envisaged. The interaction of unlabelled FtsH with other polypeptides can also be observed directly using surface plasmon resonance technology in optical biosensor devices. This method is particularly useful for measuring interactions with larger (>5 kDa) polypeptides and can be adapted to screen for inhibitors of the protein-protein interaction. Solution-based homogeneous assays using fluorescently-labelled components may be configured to report on changes in fluorescence intensity, fluorescence anisotropy, fluorescence energy transfer or correlation fluctuations in intensity as a result of the binding interaction. Binding proteins useful in these types of assay may be identified by 'ligand fishing' using, for example, optical biosensor methods and bacterial extracts followed by affinity capture or chromatography on immobilised FtsH. Optionally, derivatives of FtsH with amino acid sequences altered to improve aqueous solubility may be employed. Solution-phase capture of FtsH binding proteins may be carried out by mixing soluble FtsH with, for example, a detergent extract and reisolating a complex by use of anti- FtsH antibodies or by tagging the FtsH with, for example, Biotin and capture on immobilised avidin or streptavidin. Following elution of binding proteins from immobilised FtsH using salt, pH changes or chaotropic agents, the eluted protein products may be separated using high-resolution methods such as reverse-phase high performance liquid chromatography and the individual polypeptides characterised by N-terminal amino acid sequencing and/or mass mapping (mass spectrometry combined with molecular ion weight matching against a protein database).

(3) Nucleoside 5'-triphosphate Binding and 5'-triphosphatase Activity. The binding of nucleoside 5'-triphosphates (NTPs), such as adenosine 5'-triphosphate (ATP) to, and the subsequent hydrolysis by, FtsH protein provides for two potential in vitro assay formats. Nucleotide binding assays may be based on homogeneous or heterogeneous measurements and using radioactively labelled nucleotide (photoaffinity cross linking, gel filtration, filter binding) and using a molecular optical signal to report upon, and monitor the extent of, the binding of nucleotide or of a fluorescent/chromophoric nucleotide derivative (fluorescence intensity, anisotropy, fluctuation correlation and energy transfer measurements, absorbance and circular dichroism measurements). The ability of FtsH protein, either in the presence or absence of additional cofactors, to catalyse nucleotide hydrolysis is monitored by the change in substrate (NTP) and/or product (NDP, inorganic phosphate) concentration using either direct (radioactivity, colourimetric) or coupled enzyme formats.

(4) Microsocopy: pure FtsH protein is used to raise antibodies in mice or rabbits or other suitable animal host, which antibodies are conjugated to gold particles attached to a secondary antibody. Actively dividing cells are sampled, the gold conjugate is added, and the sample prepared for electron microscopy using standard techniques and visualise to see the localisation of the protein and any effect of test drug.

What is claimed is:

1. An isolated polynucleotide segment comprising nucleic acid sequence comprising nucleotides 1 to 2091 of the polynucleotide sequence set forth in SEQ ID NO:1, or the full complement of the entire length of the nucleic acid sequence; wherein the nucleic acid sequence or the full complement thereof is not genomic DNA.

2. An isolated polynucleotide segment comprising a first polynucleotide sequence which encodes a polypeptide comprising the amino acid sequence of SEQ ID NO:2; wherein the first polynucleotide sequence is not genomic DNA.

3. A vector comprising the isolated polynucleotide segment of claim 2.

4. An isolated host comprising the vector of claim 3.

5. A process for producing a polypeptide comprising culturing the host cell of claim 4 under conditions sufficient for the production of said polypeptide wherein the polypeptide comprises SEQ ID NO:2.

6. An isolated polynucleotide segment, comprising a first polynucleotide sequence or the full complement of the entire length of the first polynucleotide sequence, wherein the first polynucleotide sequence hybridizes to the full complement of SEQ ID NO:1, wherein the hybridization conditions include incubation at 42° C. in a solution comprising: 50% formamide, 5×SSC (150 mM NaCl, 15 mM trisodium citrate), 50 mM sodium phosphate (pH7.6), 5×Denhard's solution, 10% dextran sulfate, and 20 micrograms/ml denatured, sheared salmon sperm DNA, followed by washing in 0.1×SSC at 65° C.; wherein the first polynucleotide sequence is at least 95% identical to SEQ ID NO:1; wherein the first polynucleotide sequence or the full complement thereof is not genomic DNA and wherein the first polynucleotide sequence or the full complement thereof detects *Staphylococcus aureus* by hybridization.

7. A vector comprising the isolated polynucleotide segment of claim 6.

8. An isolated host cell comprising the vector of claim 7.

9. An isolated polynucleotide segment comprising a first polynucleotide sequence or the full complement of the entire length of the first polynucleotide sequence, wherein the first polynucleotide sequence encodes a polypeptide consisting of the amino acid sequence of SEQ ID NO:2; and wherein the first polynucleotide sequence or the full complement thereof is not genomic DNA.

10. A vector comprising the isolated polynucleotide segment of claim 9.

11. An isolated host cell comprising the vector of claim 10.

12. A process for producing a polypeptide comprising culturing the host cell of claim 11 under conditions sufficient for the production of said polypeptide, wherein the polypeptide consists of SEQ ID NO:2.

13. The isolated polynucleotide segment of claim 6, wherein the first polynucleotide sequence is at least 97% identical to SEQ ID NO:1.

14. A vector comprising the isolated polynucleotide segment of claim 13.

15. An isolated host cell comprising the vector of claim 14.

16. An isolated polynucleotide segment comprising a first polynucleotide sequence or the full complement of the entire length of the first polynucleotide sequence, wherein the first polynucleotide sequence is at least 95% identical to SEQ ID NO:1, and wherein the first polynucleotide sequence or the full complement thereof is not genomic DNA; and wherein the first polynucleotide sequence or the full complement thereof detects *Streptococcus pneumoniae* by hybridization.

17. A vector comprising the isolated polynucleotide segment of claim 16.

18. An isolated host cell comprising the vector of claim 17.

19. The isolated polynucleotide segment of claim 16, wherein the first polynucleotide sequence is at least 97% identical to SEQ ID NO:1.

20. A vector comprising the isolated polynucleotide segment of claim 19.

21. An isolated host cell comprising the vector of claim 20.

22. The isolated polynucleotide segment of claim 16, wherein the first polynucleotide sequence is at least 98% identical to SEQ ID NO:1.

23. A vector comprising the isolated polynucleotide segment of claim 22.

24. An isolated host cell comprising the vector of claim 23.

25. The isolated polynucleotide segment of claim 16, wherein the first polynucleotide sequence is at least 99% identical to SEQ ID NO:1.

26. A vector comprising the isolated polynucleotide segment of claim 25.

27. An isolated host cell comprising the vector of claim 26.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2094 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

```
ATGCAGAAAG CTTTTCGCAA TGTGCTAGTT ATCGTAATAA TAGGCGTTAT TATTTTTGGT      60

CTATTTTCAT ATTTAAACGG TAATGGAAAT ATGCCGAAAC AGCTTACATA TAATCAATTT     120

ACTGAGAAGT TGGAAAAAGG TGACCTTAAA ACTTTAGAAA TCCAACCACA ACAAAATGTC     180

TATATGGTAA GTGGTAAAAC GAAAAATGAT GAAGACTATT CATCAACTAT TTTATATAAC     240
```

-continued

```
AACGAAAAAG AATTACAAAA AATTACTGAT GCTGCTAAAA AGCAAAACGG TGTAAAATTA    300

ACGATTAAAG AAGAAGAAAA ACAAAGTGTC TTTGTGAGTA TACTTTCAAC ATTAATTCCA    360

GTTGTAGTCA TAGCGTTATT ATTTATTTTC TTCCTAAGCC AAGCACAAGG TGGCGGTAGT    420

GGCGGTCGTA TGATGAACTT TGGTAAATCT AAAGCAAAAA TGTACGATAA TAATAAACGT    480

CGTGTTCGTT TCTCTGATGT AGCAGGGGCA GATGAAGAAA ACAAGAATT AATTGAAATT    540

GTTGATTTCT TGAAAGATAA TAAAAAATTC AAAGAAATGG GATCTAGGAT TCCTAAAGGT    600

GTCTTACTTG TTGGACCTCC AGGTACTGGT AAAACATTAC TTGCTAGAGC GGTTGCAGGT    660

GAAGCTGGCG CACCATTCTT CTCTATTAGT GGTTCAGACT TTGTAGAGAT GTTTGTTGGT    720

GTTGGTGCGA GCCGTGTTCG TGACTTATTC GATAATGCTA AGAAAAACGC GCCTTGTATC    780

ATCTTTATCG ATGAGATTGA TGCTGTTGGT CGTCAACGTG GTGCAGGTGT TGGTGGCGGT    840

CATGATGAAC GTGAACAAAC CCTAAACCAA TTATTAGTTG AAATGGATGG TTTCGGTGAA    900

AATGAAGGTA TCATTATGAT AGCTGCTACA AACCGTCCTG ATATCCTTGA CCCAGCCTTA    960

TTACGTCCAG GTCGTTTTGA TAGACAAATT CAAGTTGGTC GTCCAGATGT GAAAGGCCGT   1020

GAAGCAATTC TTCATGTTCA TGCTAAAAAC AAACCACTTG ATGAAACGGT TGATTTAAAA   1080

GCAATTTCAC AACGTACACC TGGTTTCTCA GGTGCTGATT TAGAGAACTT ATTAAATGAA   1140

GCATCTTTAA TTGCTGTACG TGAAGGTAAA AAGAAAATTG ACATGAGAGA TATCGAAGAG   1200

GCAACGGATA GAGTTATAGC CGGACCTGCT AAGAAATCTC GAGTTATTTC TAAGAAAGAA   1260

CGTAATATTG TTGCTCATCA CGAAGCTGGT CATACAATTA TCGGTATGGT ACTTGATGAG   1320

GCAGAAGTAG TGCATAAAGT TACTATTGTT CCACGTGGAC AAGCAGGTGG TTATGCAATG   1380

ATGCTACCTA AACAAGATCG TTTCTTAATG ACTGAACAAG AGTTATTAGA TAAAATCTGT   1440

GGTTTACTTG GTGGACGTGT ATCAGAAGAT ATTAACTTTA ACGAAGTATC AACAGGTGCT   1500

TCAAATGACT TCGAACGTGC AACACAAATC GCACGCTCAA TGGTTACGCA ATATGGTATG   1560

AGTAAAAAAT TAGGACCATT ACAGTTCGGT CATAGCAATG GTCAAGTATT CTTAGGTAAA   1620

GATATGCAAG GTGAGCCTAA TTATTCAAGC CAAATCGCAT ATGAAATTGA TAAAGAAGTT   1680

CAACGAATCG TTAAAGAACA ATACGAACGT TGTAAACAAA TTTTATTAGA GCACAAAGAA   1740

CAATTAATTT TAATTGCTGA AACATTATTA ACAGAAGAAA CATTAGTTGC TGAACAAATT   1800

CAATCATTAT TCTACGAAGG TAAATTACCT GAAATTGATT ATGATGCAGC TAAAGTTGTT   1860

AAAGATGAAG ATTCTGAATT TAATGATGGT AAATTCGGTA AATCTTATGA AGAGATTCGT   1920

AAAGAGCAAT TAGAAGATGG ACAACGTGAC GAAAGTGAAG ATCGTAAAGA AGAAAAAGAT   1980

ATTGCTGAGG ATAAAAAAGA AGCTGATAAA TCTGATGAAA AAGATGAACC AGCACATCGA   2040

CAAGCCCCAA ATATCGAAAA ACCTTACGAT CCAAATCACC CAGACAATAA ATAA         2094
```

(2) INFORMATION FOR SEQ ID NO:2:

(i) SEQUENCE CHARACTERISTICS:
        (A) LENGTH: 697 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gln Lys Ala Phe Arg Asn Val Leu Val Ile Val Ile Gly Val
 1               5                  10                  15

Ile Ile Phe Gly Leu Phe Ser Tyr Leu Asn Gly Asn Gly Asn Met Pro
```

```
                20                  25                  30
Lys Gln Leu Thr Tyr Asn Gln Phe Thr Glu Lys Leu Glu Lys Gly Asp
             35                  40                  45

Leu Lys Thr Leu Glu Ile Gln Pro Gln Gln Asn Val Tyr Met Val Ser
 50                  55                  60

Gly Lys Thr Lys Asn Asp Glu Asp Tyr Ser Ser Thr Ile Leu Tyr Asn
65                  70                  75                  80

Asn Glu Lys Glu Leu Gln Lys Ile Thr Asp Ala Lys Lys Gln Asn
                 85                  90                  95

Gly Val Lys Leu Thr Ile Lys Glu Glu Lys Gln Ser Val Phe Val
                100                 105                 110

Ser Ile Leu Ser Thr Leu Ile Pro Val Val Ile Ala Leu Leu Phe
             115                 120                 125

Ile Phe Phe Leu Ser Gln Ala Gln Gly Gly Ser Gly Gly Arg Met
         130                 135                 140

Met Asn Phe Gly Lys Ser Lys Ala Lys Met Tyr Asp Asn Asn Lys Arg
145                 150                 155                 160

Arg Val Arg Phe Ser Asp Val Ala Gly Ala Asp Glu Glu Lys Gln Glu
                165                 170                 175

Leu Ile Glu Ile Val Asp Phe Leu Lys Asp Asn Lys Lys Phe Lys Glu
             180                 185                 190

Met Gly Ser Arg Ile Pro Lys Gly Val Leu Leu Val Gly Pro Pro Gly
         195                 200                 205

Thr Gly Lys Thr Leu Leu Ala Arg Ala Val Ala Gly Glu Ala Gly Ala
    210                 215                 220

Pro Phe Phe Ser Ile Ser Gly Ser Asp Phe Val Glu Met Phe Val Gly
225                 230                 235                 240

Val Gly Ala Ser Arg Val Arg Asp Leu Phe Asp Asn Ala Lys Lys Asn
                245                 250                 255

Ala Pro Cys Ile Ile Phe Ile Asp Glu Ile Asp Ala Val Gly Arg Gln
             260                 265                 270

Arg Gly Ala Gly Val Gly Gly Gly His Asp Glu Arg Glu Gln Thr Leu
         275                 280                 285

Asn Gln Leu Leu Val Glu Met Asp Gly Phe Gly Glu Asn Glu Gly Ile
    290                 295                 300

Ile Met Ile Ala Ala Thr Asn Arg Pro Asp Ile Leu Asp Pro Ala Leu
305                 310                 315                 320

Leu Arg Pro Gly Arg Phe Asp Arg Gln Ile Gln Val Gly Arg Pro Asp
                325                 330                 335

Val Lys Gly Arg Glu Ala Ile Leu His Val His Ala Lys Asn Lys Pro
             340                 345                 350

Leu Asp Glu Thr Val Asp Leu Lys Ala Ile Ser Gln Arg Thr Pro Gly
         355                 360                 365

Phe Ser Gly Ala Asp Leu Glu Asn Leu Leu Asn Glu Ala Ser Leu Ile
    370                 375                 380

Ala Val Arg Glu Gly Lys Lys Ile Asp Met Arg Asp Ile Glu Glu
385                 390                 395                 400

Ala Thr Asp Arg Val Ile Ala Gly Pro Ala Lys Lys Ser Arg Val Ile
                405                 410                 415

Ser Lys Lys Glu Arg Asn Ile Val Ala His His Glu Ala Gly His Thr
             420                 425                 430

Ile Ile Gly Met Val Leu Asp Glu Ala Glu Val Val His Lys Val Thr
         435                 440                 445
```

```
Ile Val Pro Arg Gly Gln Ala Gly Gly Tyr Ala Met Met Leu Pro Lys
    450                 455                 460
Gln Asp Arg Phe Leu Met Thr Glu Gln Glu Leu Leu Asp Lys Ile Cys
465                 470                 475                 480
Gly Leu Leu Gly Gly Arg Val Ser Glu Asp Ile Asn Phe Asn Glu Val
                485                 490                 495
Ser Thr Gly Ala Ser Asn Asp Phe Glu Arg Ala Thr Gln Ile Ala Arg
                500                 505                 510
Ser Met Val Thr Gln Tyr Gly Met Ser Lys Lys Leu Gly Pro Leu Gln
            515                 520                 525
Phe Gly His Ser Asn Gly Gln Val Phe Leu Gly Lys Asp Met Gln Gly
    530                 535                 540
Glu Pro Asn Tyr Ser Ser Gln Ile Ala Tyr Glu Ile Asp Lys Glu Val
545                 550                 555                 560
Gln Arg Ile Val Lys Glu Gln Tyr Glu Arg Cys Lys Gln Ile Leu Leu
                565                 570                 575
Glu His Lys Glu Gln Leu Ile Leu Ile Ala Glu Thr Leu Leu Thr Glu
                580                 585                 590
Glu Thr Leu Val Ala Glu Gln Ile Gln Ser Leu Phe Tyr Glu Gly Lys
            595                 600                 605
Leu Pro Glu Ile Asp Tyr Asp Ala Ala Lys Val Val Lys Asp Glu Asp
    610                 615                 620
Ser Glu Phe Asn Asp Gly Lys Phe Gly Lys Ser Tyr Glu Glu Ile Arg
625                 630                 635                 640
Lys Glu Gln Leu Glu Asp Gly Gln Arg Asp Glu Ser Glu Asp Arg Lys
                645                 650                 655
Glu Glu Lys Asp Ile Ala Glu Asp Lys Lys Glu Ala Asp Lys Ser Asp
                660                 665                 670
Glu Lys Asp Glu Pro Ala His Arg Gln Ala Pro Asn Ile Glu Lys Pro
            675                 680                 685
Tyr Asp Pro Asn His Pro Asp Asn Lys
    690                 695
```